United States Patent
Gotta et al.

(10) Patent No.: US 6,768,032 B2
(45) Date of Patent: Jul. 27, 2004

(54) CONTINUOUS ISOTHERMAL PROCESS FOR PREPARING MONONITROTOLUENES IN THE PRESENCE OF PHOSPHORIC ACID

(75) Inventors: Matthias Gotta, Köln (DE); Ralf Demuth, Hilden (DE); Eberhard Zirngiebl, Köln (DE); Hans-Martin Weber, Leverkusen (DE); Georg Ronge, Düsseldorf (DE)

(73) Assignee: Bayer Chemicals AG, Leverkusen (DE)

( * ) Notice: Subject to any disclaimer, the term of this patent is extended or adjusted under 35 U.S.C. 154(b) by 0 days.

(21) Appl. No.: 10/114,288

(22) Filed: Apr. 2, 2002

(65) Prior Publication Data

US 2002/0147372 A1 Oct. 10, 2002

(30) Foreign Application Priority Data

Apr. 6, 2001 (DE) .......................................... 101 17 207

(51) Int. Cl.[7] ............................................ C07C 205/00
(52) U.S. Cl. ........................................ 568/940; 568/939
(58) Field of Search ................................. 568/939, 940

(56) References Cited

U.S. PATENT DOCUMENTS

| | | | |
|---|---|---|---|
| 3,488,397 A | 1/1970 | Hakansson et al. ......... 260/645 |
| 4,772,757 A | 9/1988 | Lailach et al. .............. 568/939 |
| 5,275,701 A | * | 1/1994 | Mazzafro et al. ............. 203/12 |
| 5,763,697 A | 6/1998 | Hermann et al. ........... 568/939 |
| 2002/0091290 A1 | 7/2002 | Demuth et al. ............. 568/940 |

OTHER PUBLICATIONS

Industrial and Laboratory Nitrations, (month unavailable), 1976, Lyle F. Albright, Editor and Carl Hanson, Editor, pp. 300–312, G.F.P. Harris, Isomer Control in the Mononitration of Toluene.

Nitration: Methods and Mechanisms, (month unavailble) 1989, pp. 15–18, Olah et al, Acid–Catalyzed Electrophilic Nitration.

* cited by examiner

Primary Examiner—J. Parsa
(74) Attorney, Agent, or Firm—Godffied R. Akorli; Diderico van Eyl

(57) ABSTRACT

The present invention relates to a continuous isothermal process for preparing mononitrotoluenes in the presence of a mixed acid component comprising mixtures of sulfuric acid and phosphoric acid with concentration of the resultant waste acid and recycling of the concentrated waste acid to the process.

16 Claims, No Drawings

CONTINUOUS ISOTHERMAL PROCESS FOR PREPARING MONONITROTOLUENES IN THE PRESENCE OF PHOSPHORIC ACID

BACKGROUND

The present invention relates to a continuous isothermal process for preparing mononitrotoluenes using mixtures of sulfuric acid and phosphoric acid. The resultant waste acid is subjected to a concentration integrated into the process and is then recycled to the process.

Mononitrotoluenes are important intermediates for preparing optical brighteners, crop protection agents and pharmaceutical products. They can be prepared on an industrial scale, for example, by isothermal nitration of toluene. In this case, toluene is reacted with a mixture of sulfuric acid and nitric acid (mixed acid, nitrating acid) (Kirk-Othmer, Encyclopedia of Chemical Technology Vol. 17, 4th Edition 1996, "Nitration" and "Nitrobenzenes and Nitrotoluene").

When nitrations are performed in pure sulfuric acid, customarily a ratio of o-nitrotoluene to para-nitrotoluene of approximately 1.65 is obtained (Albright & Hanson, Industrial and Laboratory Nitrations, 1976, pp. 300–312). Replacing sulfuric acid by pure phosphoric acid leads to a shifting of this ratio towards a greater fraction of the para isomer (Olah et al., Methods and Mechanisms, 1989, pp. 15–18). However, owing to the reduced acid strength of phosphoric acid, compared with sulfuric acid, when it is used there is customarily greater retardation of the reaction. To achieve comparable reaction rates, therefore, the use of highly concentrated polyphosphoric acids is recommended, which can be prepared from the addition of $P_2O_5$ to orthophosphoric acid.

DE 164 36 00 A assesses this procedure, in that reference is made to the problems associated with the use of polyphosphoric acids with respect to their corrosivity towards materials customary in industry.

DE 164 36 00 A discloses in this respect process parameters for nitrating toluene in phosphoric acid, where the use of a 100.8% strength phosphoric acid leads to an o/p-nitrotoluene ratio of 0.90. However, the high excesses of mixed acid used in the examples and the long reaction times given indicate a low space-time yield to those skilled in the art, which makes economic utilization of the proposed process appear doubtful.

Typically in DE 164 36 00 A, an approximately 97% strength phosphoric acid is obtained at the reactor outlet. The concentration step required for recycling this waste acid requires evaporating the reaction water at temperatures of approximately 180° C. at a pressure of approximately 20 mbar, as may be taken from the boiling diagram of the $H_2O$—$H_3PO_4$ system. These parameters may only be achieved with considerable expenditure both with respect to the materials used and with respect to equipment requirements and thus obstruct economically advantageous use of pure phosphoric acid as a mixed acid component. Thus, for example, the isocorrosion curves of enamel under these process conditions mean that no resistance to a phosphoric acid of this concentration may be expected.

DE 164 36 00 A additionally develops a process alternative in which sulfuric acid is added to the mixed acid in an amount of up to 80% of the phosphoric acid used. This addition of sulfuric acid, compared with the procedure in pure phosphoric acid, does not lead to a significant shift of the isomer ratio towards the ortho isomer. Nevertheless, it does not indicate to those skilled in the art a solution of the problems occurring with the use of pure phosphoric acid, since the drastic process conditions to concentrate waste acid, the increased corrosivity of the acid towards customary materials, and the low space-time yield further counteract industrial implementation of a process to be used with economic advantage.

Industrial processes for the mononitration of toluene using mixed acid are associated with the production of waste acids which are contaminated with considerable proportions of organic compounds, for example dinitrotoluenes, or nitrated cresols, and must be worked up in a process- and cost-intensive manner.

Thus, for example, in the case of nitration with the use of pure sulfuric acid, processes have been developed which comprise concentrating sulfuric acid, with the concentrated sulfuric acid being freed from water and organic compounds, then recycled back to the nitration reaction in a circulation process, and thus avoiding the production of waste acid.

DE 195 39 205 A discloses process parameters for the mononitration of aromatics, with the mixed acids being matched to the properties of the aromatics to be nitrated in such a manner as to produce an approximately 70% strength waste sulfuric acid. In addition, the use of partially concentrated waste acids having a sulfuric acid concentration between 85% and 92% is described.

U.S. Pat. No. 4,772,757 describes a process for preparing nitrobenzene in which the waste acid produced is concentrated to 75 to 92% and is recirculated back to the nitration process. Since toluene is markedly more sensitive to oxidation compared with benzene, owing to the methyl group, and has a tendency in nitration to form by-products, when reaction conditions for nitrating benzene are applied to the nitration of toluene, an increase in the amount of unwanted by-products may be expected.

Owing to the solubility of organic compounds in inorganic acids, organic by-products such as oxalic acid or benzoic acid accumulate in concentrated waste acids, which are recirculated to the nitration reaction. In addition, enrichment in nitrosylsulfuric acid can occur. The decomposition of these by-products and the heat of decomposition released in the course of this can lead to unwanted decomposition of the reaction product of nitrotoluene.

Furthermore, the space-time yield is impaired, since the organic by-products can react with the nitric acid used in oxidative degradation reactions and thus some of the nitric acid is no longer available for the actual nitration.

There was therefore a requirement for a continuous isothermal process for preparing mononitrotoluene having an increased yield of para-nitrotoluene by using mixtures of sulfuric acid and phosphoric acid, in which the process permits inexpensive concentration of the waste acid with subsequent recycling to the nitration reaction within the meaning of a cyclic process, without organic by-products accumulating in the concentrated acid. In addition, the use of dilute nitric acid of 60–70% by weight is desirable, since this leads to marked cost reduction compared with the use of highly concentrated nitric acid.

SUMMARY

The invention relates to a continuous process for preparing mononitrotoluenes comprising feeding toulene, nitric acid, and a mixed acid component into a reactor and reacting, under isothermal reaction conditions, the toluene with the nitric acid and the mixed acid component, wherein the mixed acid component comprises from about 45 to about 80% sulfuric acid, from about 9 to about 45% phosphoric acid and from about 5 to about 15% water. These and other features, aspects, and advantages of the present invention will become better understood with reference to the following description and appended claims.

DESCRIPTION

A continuous process has been found for preparing mononitrotoluenes by reacting toluene with nitric acid, sulfuric acid and phosphoric acid under isothermal reaction conditions, which is characterized in that mixtures of sulfuric acid and phosphoric acid are used as mixed acid component, which mixtures comprise from about 45 to about 80% sulfuric acid, from about 9 to about 45% phosphoric acid and from about 5 to about 15% water.

A particularly preferred embodiment of the inventive process is characterized in that mixtures of sulfuric acid and phosphoric acid are used as mixed acid component, which mixtures are composed of from about 64 to about 78% sulfuric acid, from about 10 to about 27% phosphoric acid and from about 8 to about 13% water.

A particular embodiment of the inventive process is characterized in that, in a subsequent step, the mixed acid component and from about 60 to about 70% strength nitric acid and toluene are fed into the reactor. The inventive process is characterized in that mixed acid component and from about 60 to about 70% strength nitric acid are fed into the reactor in a weight ratio of from about 2:1 to about 4:1, based on nitric acid, and mixed acid component and toluene are fed into the reactor in a weight ratio of from about 2:1 to about 4:1 based on toluene.

A particularly preferred embodiment of the inventive process is characterized in that in a subsequent step the mixed acid component and from about 60 to about 70% strength nitric acid and toluene are fed into the reactor. The inventive process is characterized in that mixed acid component and from about 60 to about 70% strength nitric acid are fed into the reactor in a weight ratio of from about 2.4:1 to about 3.3:1 based on nitric acid, and mixed acid component and toluene are fed into the reactor in a weight ratio of from about 2.4:1 to about 3.2:1 based on toluene.

A particular embodiment of the inventive process is characterized in that in a subsequent step the crude nitrotoluene is separated from the waste acid at the reactor outlet.

A particular embodiment of the inventive process is characterized in that the waste acid at the reactor outlet comprises from about 42 to about 70% sulfuric acid, from about 6 to about 37% phosphoric acid and from about 15 to about 28% water. The waste acid is virtually free from nitric acid and can in addition comprise organic compounds, for example dinitrotoluenes or nitrated cresols, and if appropriate nitrous acid.

A particularly preferred embodiment of the inventive process is characterized in that the waste acid at the reactor outlet comprises from about 54 to about 67% sulfuric acid, from about 7 to about 22% phosphoric acid and from about 18 to about 27% water.

A particular embodiment of the inventive process is characterized in that in a subsequent step, the waste acid is subjected to a single-stage concentration to a composition of from about 45 to about 80% sulfuric acid, from about 9 to about 45% phosphoric acid and from about 5 to about 15% water.

A particularly preferred embodiment of the inventive process is characterized in that the waste acid is subjected to a single-stage concentration to a composition of from about 64 to about 78% sulfuric acid, from about 10 to about 27% phosphoric acid and from about 8 to about 13% water.

A particular embodiment of the inventive process is characterized in that, in a subsequent step, the concentrated waste acid is recycled back to the nitration reaction in a circuit.

A particular embodiment of the inventive process is characterized in that
a) mixtures of sulfuric acid and phosphoric acid as mixed acid component are used, which mixtures comprise from about 45 to about 80% sulfuric acid, from about 9 to about 45% phosphoric acid and from about 5 to about 15% water,
b) the mixed acid component, from about 60 to about 70% strength nitric acid and toluene are fed into a reactor, mixed acid component and nitric acid being in a weight ratio of from about 2:1 to about 4:1, based on nitric acid, and mixed acid component and toluene being in a weight ratio of from about 2:1 to 4:1, based on toluene,
c) the crude nitrotoluene is separated from the waste acid at the reactor outlet,
d) the waste acid which comprises from about 42 to about 70% sulfuric acid, from about 6 to about 37% phosphoric acid and from about 15 to about 28% water is concentrated in a single-stage concentration to a composition of from about 45 to about 80% sulfuric acid, from about 9 to about 45% phosphoric acid and from about 5 to about 15% water and
e) the concentrated waste acid is recycled back to the nitration reaction in a circuit.

A particularly preferred embodiment of the inventive process is characterized in that
a) mixtures of sulfuric acid and phosphoric acid as mixed acid component are used, which mixtures comprise from about 64 to about 78% sulfuric acid, from about 10 to about 27% phosphoric acid and from about 8 to about 13% water,
b) the mixed acid component, from about 60 to about 70% strength nitric acid and toluene are fed into a reactor, mixed acid component and nitric acid being in a weight ratio of from about 2.4:1 to about 3.3:1 based on nitric acid, and mixed acid component and toluene being in a weight ratio of from about 2.4:1 to about 3.2:1 based on toluene,
c) the crude nitrotoluene is separated from the waste acid at the reactor outlet,
the waste acid which comprises from about 54 to about 67% sulfuric acid, from about 7 to about 22% phosphoric acid and from about 18 to about 27% water is concentrated in a single-stage concentration to a composition of from about 64 to about 78% sulfuric acid, from about 10 to about 27% phosphoric acid and from about 8 to about 13% water and
d) the concentrated waste acid is recycled back to the nitration reaction in a circuit.

The inventive process, compared with the nitration in pure sulfuric acid which is customary in industry, surprisingly leads to an increased content of para-nitrotoluene at an already small content of phosphoric acid as mixed acid component. Para-nitrotoluene has particular interest as the intermediate for preparing optical brighteners, active compounds for pharmacy and agriculture, and dyes and fragrances.

In the inventive process, advantageously, a dilute nitric acid is used, as a result of which the process can be operated particularly inexpensively. Despite relatively high amounts of water, due to the use of dilute nitric acid, the reaction proceeds at high reaction rates. The reaction rate essentially depends in the inventive process on the concentration of the sulfuric acid used. The amount of phosphoric acid used thus serves primarily to control the isomeric ratio.

In the inventive process, preferably, from about 0.98 to about 1.1 equivalents of toluene based on one equivalent of nitric acid are used, particularly preferably from about 1.01 to about 1.05 equivalents of toluene are used based on one equivalent of nitric acid. Even if there is a toluene excess based on nitric acid, in the inventive process, surprisingly, no increase in impurities occurs.

The starting materials nitric acid, sulfuric acid, phosphoric acid and toluene used in the inventive process are preferably intensively mixed using mixing elements known in industry. The mixing elements which can be used are, for example, static mixers, pumps, nozzles, agitators or combinations of the said mixing elements.

The inventive process is carried out continuously under isothermal conditions in a reactor. The reactors used are preferably commercially available reactors, for example tubular reactors, loop reactors, stirred tanks, or else combinations of loop reactors and stirred tanks. In a further preferred embodiment, the inventive process is carried out in multistage reactor cascades.

The inventive process is carried out under isothermal conditions, the reaction temperature preferably being in the range from about 20 to about 80° C., particularly preferably in the range from about 30 to about 70° C., and very particularly preferably in the range from about 40 to about 65° C.

The crude nitrotoluene is preferably separated from the waste acid using a static separator or a centrifugal separator. In this case, methods of static or dynamic phase separation known to those skilled in the art are used, for example centrifugal separators or separating flasks with and without internals.

By means of the concentration of the waste acid carried out in the inventive process, this waste acid is substantially freed from water and organic compounds, the organic compounds either being removed from the waste acid or destroyed in such a manner that volatile compounds such as $CO_2$ are formed, which are discharged from the waste acid.

The single-stage concentration is preferably carried out in an evaporator. In order to obtain the inventive composition of the sulfuric acid/phosphoric acid mixture, the evaporator is preferably operated at a pressure of from about 30 to about 300 mbar, particularly preferably from about 60 to about 200 mbar, and very particularly preferably from about 80 to about 150 mbar. The temperature of the waste acid in the evaporator exit is preferably from about 100 to about 200° C., particularly preferably from about 150 to about 190° C., and very particularly preferably from about 155 to about 185° C. The heat of the effluent concentrated waste acid is preferably used in a countercurrent flow heat exchanger to heat the waste acid flowing into the evaporator. In this case the waste acid flowing into the evaporator is preferably heated by the countercurrent flow to the extent that this waste acid is superheated at evaporator pressure and thus some of the water and small amounts of the acid vaporize without additional supply of heat (flash evaporation).

For the single-stage concentration in the inventive process, preferably an evaporator having a tantalum tube bundle, which is also commercially available, distils in a single stage and is in a cascade along its length, in which the acid concentration is increased with each cascade, starting from the inlet, so that a relatively less-concentrated acid is present in the first cascades. An advantage of the low concentration in the first cascades is, firstly, that the boiling point is still low and thus there is a high driving temperature difference for the heat transfer (smaller evaporator) and, secondly, that at low acid concentrations any nitrosylsulfuric acid present in the waste acid can readily be removed from the reaction. Thus, by using a single-stage cascade-type evaporator in the inventive process, expelling the nitrosylsulfuric acid by blowing with sulfur dioxide, and thus an additional process step, is avoided.

Preferably, a stripping section is used in order to achieve particularly good reduction in content of organic compounds and/or content of nitrosylsulfuric acid. A distillation column section equipped with distillation internals is termed the stripping section, to which the waste acid, which is liquid or somewhat superheated at evaporator pressure, is passed from the top and which is operated in countercurrent from the bottom by the vapor ascending from the evaporator. Distillation internals which can be used in the stripping section are column internals known to those skilled in the art, for example trays, arranged packings and random packings. In a preferred embodiment, low-pressure drop distillation internals such as arranged packings or random packings are used. The dwell time in the stripping section, with simultaneously low acid concentration, leads, together with the mass transfer intensified by the distillation internals, advantageously to rapid decomposition and separation of organic and inorganic compounds.

The crude nitrotoluene obtained in the inventive process generally comprises less than about 0.5% of dinitrated compounds and less than about 0.8% dinitrocresols.

In the inventive process, a substream can be taken off in order to avoid, if appropriate, concentrating by-products in the acid circuit.

In the inventive process there is the possibility of also using as starting material toluene having a low content of dinitrotoluenes and nitrated cresols.

In the inventive process there is the possibility of preventing attack on the materials used by the mixed acid component comprising sulfuric acid/phosphoric acid by adding up to about 2,000 ppm of water glass to this.

The invention is further described in the following illustrative examples in which all parts and percentages are by weight unless otherwise indicated.

EXAMPLES

Example 1

In a miniplant, a stirred-tank cascade was fed with 1.03 kg of an acid of composition 75% $H_2SO_4$, 13% $H_3PO_4$ and 12% $H_2O$, 0.33 kg of 68% strength nitric acid and 0.33 kg of toluene per hour. The temperature in the stirred tanks was approximately 45° C. After completion of the reaction the crude nitrotoluene was separated from the waste acid by means of a static separator. The waste acid was fed via a preheater to an evaporator and concentrated at 100 mbar and 170° C. to 75% $H_2SO_4$, 13% $H_3PO_4$ and 12% $H_2O$, with organic compounds being distilled off or destroyed. The concentrated waste acid is fed back to the nitration reaction.

The resultant crude nitrotoluene had the following composition: 2.23% toluene, 55.88% ortho-nitrotoluene, 4.39% meta-nitrotoluene, 37.16% para-nitrotoluene, 0.31% dinitrotoluene and 0.26% dinitrocresol.

Ortho-nitrotoluene/para-nitrotoluene=1.50.

Example 2

In a miniplant, a stirred-tank cascade was fed with 1.03 kg of an acid of composition 54% $H_2SO_4$, 38% $H_3PO_4$ and 8%

H$_2$O, 0.33 kg of 68% strength nitric acid and 0.33 kg of toluene per hour. The temperature in the stirred tanks was approximately 45° C. After completion of the reaction, the crude nitrotoluene was separated from the waste acid by means of a static separator. The waste acid was fed via a preheater to an evaporator and concentrated at 100 mbar and 170° C. to 54% H$_2$SO$_4$, 38% H$_3$PO$_4$ and 8% H$_2$O, with organic compounds being distilled off or destroyed. The concentrated waste acid is fed back to the nitration reaction.

The resultant crude nitrotoluene had the following composition: 2.44% toluene, 54.99% ortho-nitrotoluene, 4.42% meta-nitrotoluene, 37.67% para- nitrotoluene, 0.19% dinitrotoluene and 0.29% dinitrocresol.

Ortho-nitrotoluene/para-nitrotoluene=1.46.

Example 3

In a miniplant, a stirred-tank cascade was fed with 1.03 kg of an acid of composition 67% H$_2$SO$_4$, 22% H$_3$PO$_4$ and 11% H$_2$O, 0.33 kg of 68% strength nitric acid and 0.33 kg of toluene per hour. The temperature in the stirred tanks was approximately 45° C. After completion of the reaction, the crude nitrotoluene was separated from the waste acid by means of a static separator. The waste acid was fed via a preheater to an evaporator and concentrated at 100 mbar and 168° C. to 67% H$_2$SO$_4$, 22% H$_3$PO$_4$ and 11% H$_2$O, with organic compounds being distilled off or destroyed. The concentrated waste acid is fed back to the nitration reaction.

The resultant crude nitrotoluene had the following composition: 2.25% toluene, 55.66% ortho-nitrotoluene, 4.36% meta-nitrotoluene, 37.24% para- nitrotoluene, 0.23% dinitrotoluene and 0.26% dinitrocresol.

Ortho-nitrotoluene/para-nitrotoluene=1.49.

Comparison Example 1

In a miniplant, a stirred-tank cascade was fed with 0.80 kg of 87.7% strength sulfuric acid, 0.31 kg of 67% strength nitric acid and 0.32 kg of toluene per hour. The temperature in the stirred tanks was approximately 40° C. After completion of the reaction the crude nitrotoluene was separated off from the waste sulfuric acid by means of a static separator. The waste sulfuric acid was fed via a preheater to an evaporator and concentrated at 100 mbar and 168° C. to 87.7%, with organic compounds being distilled off or destroyed. The waste sulfuric acid can be fed back to the nitration reaction.

The resultant crude nitrotoluene had the following composition: 3.27% toluene, 57.58% ortho-nitrotoluene, 4.13% meta-nitrotoluene, 34.68% para- nitrotoluene, 0.08% dinitrotoluene and 0.38% dinitrocresol. Ortho-nitrotoluene/para-nitrotoluene=1.66

Comparison Example 2

A cascade existing of a plurality of loop reactors were fed with 3 000 l of approximately 97% pure toluene, which contains small amounts of nitrated toluenes and cresols, 3 700 l of 87% strength sulfuric acid and 1 800 l of 67 to 68% strength nitric acid per hour. The reactors were operated between 43 and 47° C. After completion of the reaction, the crude nitrotoluene was separated off from the waste sulfuric acid by means of a centrifugal separator. The waste sulfuric acid was reconcentrated to the initial value of 87% at approximately 170° C. at 100 mbar and recycled to the nitration reaction.

The resultant crude nitrotoluene had the following composition: 4.13% toluene, 57.12% ortho-nitrotoluene, 4.18% meta-nitrotoluene, 34.17% para-nitrotoluene, 0.12% dinitrotoluene and 0.71% cresols. Ortho-nitrotoluene/para-nitrotoluene=1.67.

Compared with the inventive examples, at comparable values for the general reaction conditions, a smaller proportion of para-nitrotoluene was found, with otherwise similar by-product spectrum.

Although the present invention has been described in detail with reference to certain preferred versions thereof, other variations are possible. Therefore, the spirit and scope of the appended claims should not be limited to the description of the versions contained therein.

What is claimed is:

1. A continuous process for preparing mononitrotoluenes comprising feeding toulene, nitric acid, and a mixed acid component into a reactor and reacting, under isothermal reaction conditions, the toluene with the nitric acid and the mixed acid component, wherein the mixed acid component comprises from about 45 to about 80% sulfuric acid, from about 9 to about 45% phosphoric acid and from about 5 to about 15% water.

2. The process according to claim 1, wherein the nitric acid and toluene fed into the reactor are from about 80 to about 70% strength.

3. The process according to claim 1, wherein the reactor has a reactor outlet and crude nitrotoluene is separated from waste acid at the reactor outlet by liquid—liquid phase separation.

4. The process according to claim 3, wherein waste acid is subjected to a single-stage concentration to form a composition of concentrated waste acid comprising from about 45 to about 80% sulfuric acid, from about 9 to about 45% phosphoric acid and from about 5 to about 15% water.

5. The process according to claim 4, wherein the concentrated waste acid is recycled back to the nitration reaction in a circuit.

6. The process according to claim 1, wherein a) (i) from about 60 to about 70% strength nitric acid and toluene are fed into a reactor, (ii) crude nitrotoluene is separated from waste acid at a reactor outlet, (iii) the waste acid is concentrated in a single-stage concentration to a concentrated waste acid composition ranging from about 45 to about 80% sulfuric acid, from about 9 to about 45% phosphoric acid end from about 5 to about 15% water and (iv) the concentrated waste acid is recycled back to the reactor in a circuit to undergo a nitration reaction.

7. The process according to claim 1, wherein the mixed acid component comprises from about 64 to about 78% sulfuric acid, from about 10 to about 27% phosphoric acid and from about 8 to about 13% water.

8. The process according to claim 1, wherein the nitric acid has from about 65 to about 68% strength.

9. The process according to claim 1, wherein the toulene is present in an amount ranging from about 0.98 to about 1.1 equivalents, based on one equivalent of nitric acid.

10. The process according to claim 1, wherein the toluene is used in an amount ranging from about 1.01 to about 1.05 equivalents, based on one equivalent of nitric acid.

11. The process according to claim 1, wherein the reactor has a reactor outlet and waste acid at the reactor outlet is a composition containing from about 54 to about 67% sulfuric acid, from about 7 to about 22% phosphoric acid and from about 18 to about 27% water.

12. The process according to claim 1, wherein (i) crude nitrotoluene is separated from waste acid at a reactor outlet, (ii) waste acid is concentrated in a single-stage concentration to a concentrated waste acid composition and wherein the concentration is performed in an evaporator at a pressure ranging from about 30 to about 300 mbar and at a temperature ranging from about 100 to about 200° C.

13. The process according to claim 12, wherein the concentration is performed in a cascade-type evaporator.

14. The process according to claim 13, wherein the evaporator is operated with a stripping section.

15. The process according to claim 1, wherein the reaction temperature ranges from about 20 to about 80° C.

16. The process according to claim 1, wherein, up to 2,000 ppm of water are added to the reactor.

* * * * *